US006618616B2

(12) United States Patent
Iijima et al.

(10) Patent No.: US 6,618,616 B2
(45) Date of Patent: Sep. 9, 2003

(54) BIOELECTRICAL IMPEDANCE MEASURING APPARATUS

(75) Inventors: Takeshi Iijima, Tokyo-to (JP); Takashi Serizawa, Tokyo-to (JP)

(73) Assignee: Tanita Corporation, Tokyo (JP)

( * ) Notice: Subject to any disclaimer, the term of this patent is extended or adjusted under 35 U.S.C. 154(b) by 0 days.

(21) Appl. No.: 09/894,512

(22) Filed: Jun. 29, 2001

(65) Prior Publication Data

US 2002/0002342 A1 Jan. 3, 2002

(30) Foreign Application Priority Data

Jun. 30, 2000 (JP) ........................................ 2000-198153

(51) Int. Cl.[7] ................................................ A61B 5/05
(52) U.S. Cl. ........................ 600/547; 600/300; 600/506; 324/692; 128/921
(58) Field of Search ................................. 600/547, 300, 600/301, 548, 493, 504, 506, 372; 324/691, 692; 128/900, 903, 920, 921

(56) References Cited

U.S. PATENT DOCUMENTS

| 6,256,532 | B1 | * | 7/2001 | Cha ............................. 600/547 |
| 6,327,495 | B1 | * | 12/2001 | Iwabuchi et al. ............ 600/547 |
| 6,354,996 | B1 | * | 3/2002 | Drinan et al. ................ 600/300 |
| 6,360,124 | B1 | * | 3/2002 | Iwabuchi ..................... 600/547 |
| 6,370,425 | B1 | * | 4/2002 | Oguma ........................ 600/547 |
| 6,456,873 | B1 | * | 9/2002 | Inoue et al. ................. 600/547 |
| 6,472,888 | B2 | * | 10/2002 | Oguma et al. ............... 324/691 |
| 6,473,641 | B1 | * | 10/2002 | Kodama et al. ............. 600/547 |

FOREIGN PATENT DOCUMENTS

| EP | 1 031 317 | 8/2000 |
| JP | 62169023 | 7/1987 |
| JP | 10-174680 | 6/1998 |
| JP | 2000-135204 | 5/2000 |
| JP | 2000166890 | 6/2000 |
| WO | 99/20175 | 4/1999 |
| WO | 99/52425 | 10/1999 |

OTHER PUBLICATIONS

Related U.S. application No. 09/510,231, filed Feb. 22, 2000; Our Ref.: 58647-017.

* cited by examiner

*Primary Examiner*—Teresa Walberg
*Assistant Examiner*—Fadi H. Dahbour
(74) *Attorney, Agent, or Firm*—McDermott, Will & Emery

(57) ABSTRACT

Disclosed is a bioelectrical impedance measuring apparatus which is simplified in structure and which is easy to use. A measuring apparatus comprising a personal data input unit which is used in inputting personal data and a plurality of electrodes which are used in measuring bioelectrical impedance is improved according to the present invention in that it comprises: a memory in which the personal data are stored via said personal data input unit; and a control device which carries out a required control by using at least one selected electrode to store the personal data in said memory or to retrieve the personal data from said memory.

9 Claims, 5 Drawing Sheets

BIOELECTRICAL IMPEDANCE MEASURING APPARATUS

BACKGROUND OF THE INVENTION

1. Field of the Invention

The present invention relates to a bioelectrical impedance measuring apparatus equipped with a personal data input unit.

2. Prior Art

FIG. 8 shows a conventional body fat meter 200 equipped with a weight scale 200a (hereinafter, referred to as "body fat meter"). The body fat meter 200 includes a bioelectrical impedance measuring apparatus as one component. At the outset it is necessary that user's personal data such as adult or child, sex or height be inputted and stored in a memory preliminary to required measurements in the body fat meter 200. Entry of such personal data can be effected by using individual keys 201 to 204, which are allotted to individual users for their exclusive use. In measuring his weight and body fat percentage, the user depresses the selected individual key 201, 202, 204 or 204 by finger or tiptoe to retrieve the personal data from the memory, and then the user stands on the body fat meter 200 with his feet on electrodes A, B, C and D, which are arranged on the body fat meter 200, thus starting the required measurement.

Individual keys 201, 202, 203 or 204 to be depressed in inputting the personal data or in retrieving the same from the memory are mechanical devices which require application of significant strength of force for operation. This bothers the user more or less.

Such extra individual keys 201 to 204 are arranged on the body fat meter 200. Use of such extra parts increases the manufacturing cost accordingly, and the probability of malfunction in the body fat meter 200 caused by the frequent use of such mechanical devices.

When the body fat meter 200 is stood on the floor with its individual keys down after use, it is likely that the individual keys are pressed by the weight of the body fat meter 200, thereby vainly wasting the electric power from the battery.

SUMMARY OF THE INVENTION

In view of the above a bioelectrical impedance measuring apparatus comprising a personal data input unit which is used in inputting personal data and a plurality of electrodes which are used in measuring bioelectrical impedance is improved according to the present invention in that it comprises: a memory in which the personal data are stored via said personal data input unit; and a control device which carries out a required control by using at least one selected electrode to store the personal data in said memory or to retrieve the personal data from said memory. The electrodes take the role of said individual keys, thus eliminating the necessity of providing the apparatus with individual keys in the form of mechanical devices as in the conventional structure.

The bioelectrical impedance measuring apparatus may comprise further a power switch device responsive to a touch to any one of said electrodes for turning power on. This facilitates the operation of the apparatus.

The bioelectrical impedance measuring apparatus may comprise further a weight scale and a display, said control device being responsive to the inputting of a predetermined number in place of the height via said personal data input unit for permitting said weight scale to measure the weight alone and for permitting said display to show the so measured weight alone.

The bioelectrical impedance measuring apparatus may comprise: a bioelectrical impedance measuring circuit which measures the bioelectrical impedance appearing between selected points of a living body, on which points said electrodes are attached; a touch-sensitive switch circuit which is responsive to a touch to any one of said electrodes for making weak current flow through the touched electrode; and a mode switching device which switches the connection of said electrodes from said bioelectrical impedance measuring circuit to said touch-sensitive switch circuit or inversely.

The control device may include an internal timer for counting the length of time for which an interruption continues in the course of entry of the personal data or in the course of measurement; and the control device may be responsive to the length of time thus measured exceeding a predetermined length of time for making said electrodes to be connected to said touch-sensitive switch circuit via said mode switching device, and shutting power off.

Other objects and advantage of the present invention will be understood from the following description of some preferred embodiments, which are shown in accompanying drawings.

DETAILED DESCRIPTION OF PREFERRED EMBODIMENTS

Figure 1:
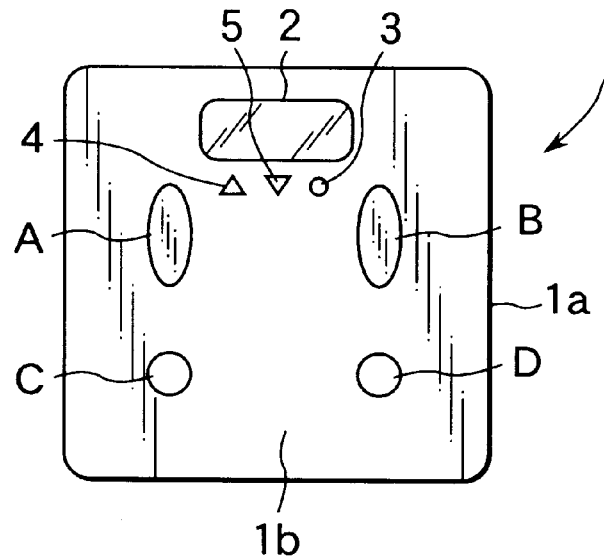
FIG. 1 shows the front view of a body fat meter according to a first embodiment of the present invention.

Now, a body fat meter according to a first embodiment of the present invention is described by referring to FIG. 1, which shows its front view. The body fat meter 1 is equipped with a weight scale 1a for measuring one's weight. A display 2, electrodes A, B, C and D, and a personal data-inputting or setting button 3 are arranged on the upper surface of the body fat meter 1. A scroll-up button 4 and a scroll-down button 5 are arranged to be adjacent to the setting button 3. The display 2 is responsive to depression of the setting button 3 for displaying a series of marks representing adult, child, male and female for selection, two of which marks, for examples, "adult" and "female" or "child" and "male" can be selected as personal data to be inputted. In addition the user's height is inputted as personal data, allowing the inputted value to be displayed. After the required measurement is finished, the weight and body fat percentage thus measured are displayed. The electrodes A, B, C and D are used in measuring bioelectrical impedance.

Figure 2:
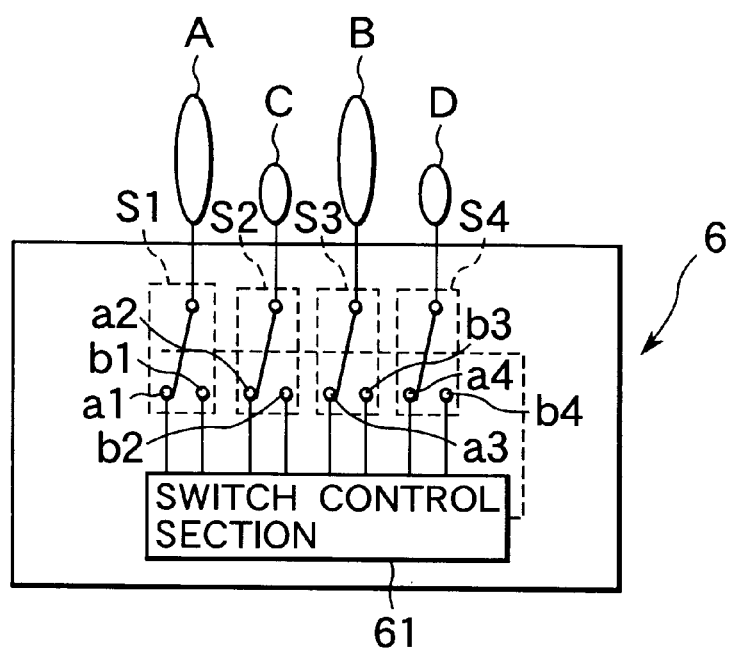
FIG. 2 shows the structure of a mode switching section of the body fat meter of FIG. 1.

FIG. 2 shows the structure of a mode switching section 6, which has a group of switch units S1 to S4 connected to the electrodes A, B, C and D and to an associated switch control section 61. In normal or stand-by mode the movable contacts of the switch units S1 to S4 are connected to the first stationary contacts a1 to a4, thereby allowing weak current to flow through any one of the electrodes A, B, C and D when touched. In body fat measuring mode the switch control section 61 makes the switches S1 to S4 move their movable contacts from the first stationary contacts a1 to a4 to the second stationary contacts b1 to b4.

Figure 3:
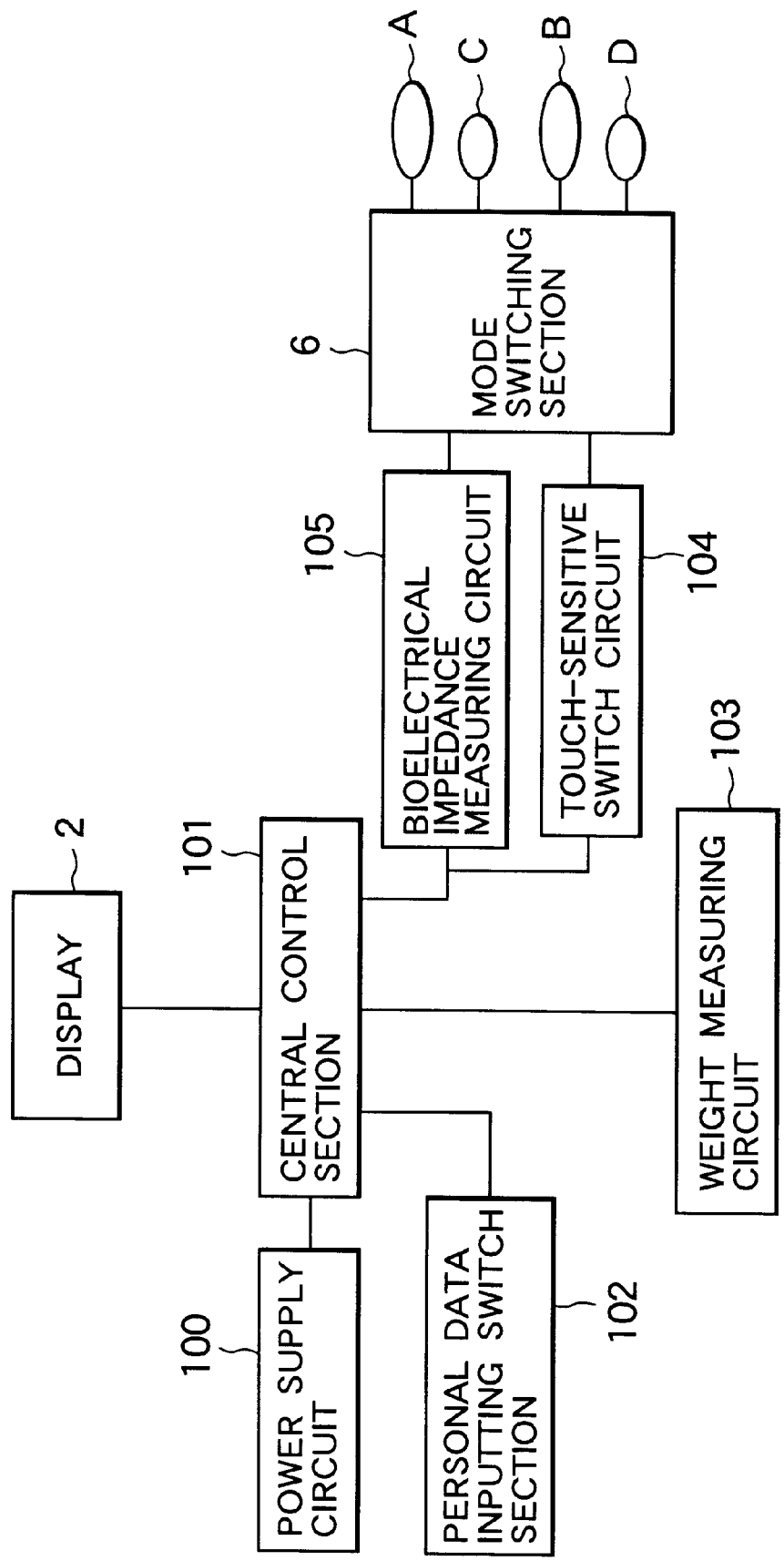
FIG. 3 shows the block diagram of a central control section and associated sections of the body fat meter of FIG. 1.

FIG. 3 shows the block diagram of a central control section 101 and associated sections of the body fat meter 1. A power supply circuit 100 is connected to the central control section 101, which includes an internal microprocessor and a memory. A personal data inputting switch section 102 includes the setting button 3, the scroll-up button 4 and the scroll-down button 5, and is connected to the central control section 101.

A weight measuring circuit 103 includes a weight-responsive strain gauge capable of providing the control section 101 with an electric signal representing one's weight. A bioelectrical impedance measuring circuit 105 is well known per se, and is capable of providing the central control section 101 with the bioelectrical impedance appearing between selected points of a living body, on which points the electrodes A, B, C and D are attached.

For the purpose the bioelectrical impedance measuring circuit 105 can be connected to the electrodes A, B, C and D via the mode switching section 6. Likewise, a touch-sensitive switch circuit 104 can be connected to the electrodes A, B, C and D via the mode switching section 6, thereby permitting detection of the touching of any one of the electrodes A, B, C and D in terms of the weak current, which flows through the electrode thus touched. Then, the touch-sensitive switch circuit 104 makes the power supply turn on.

Figure 4:
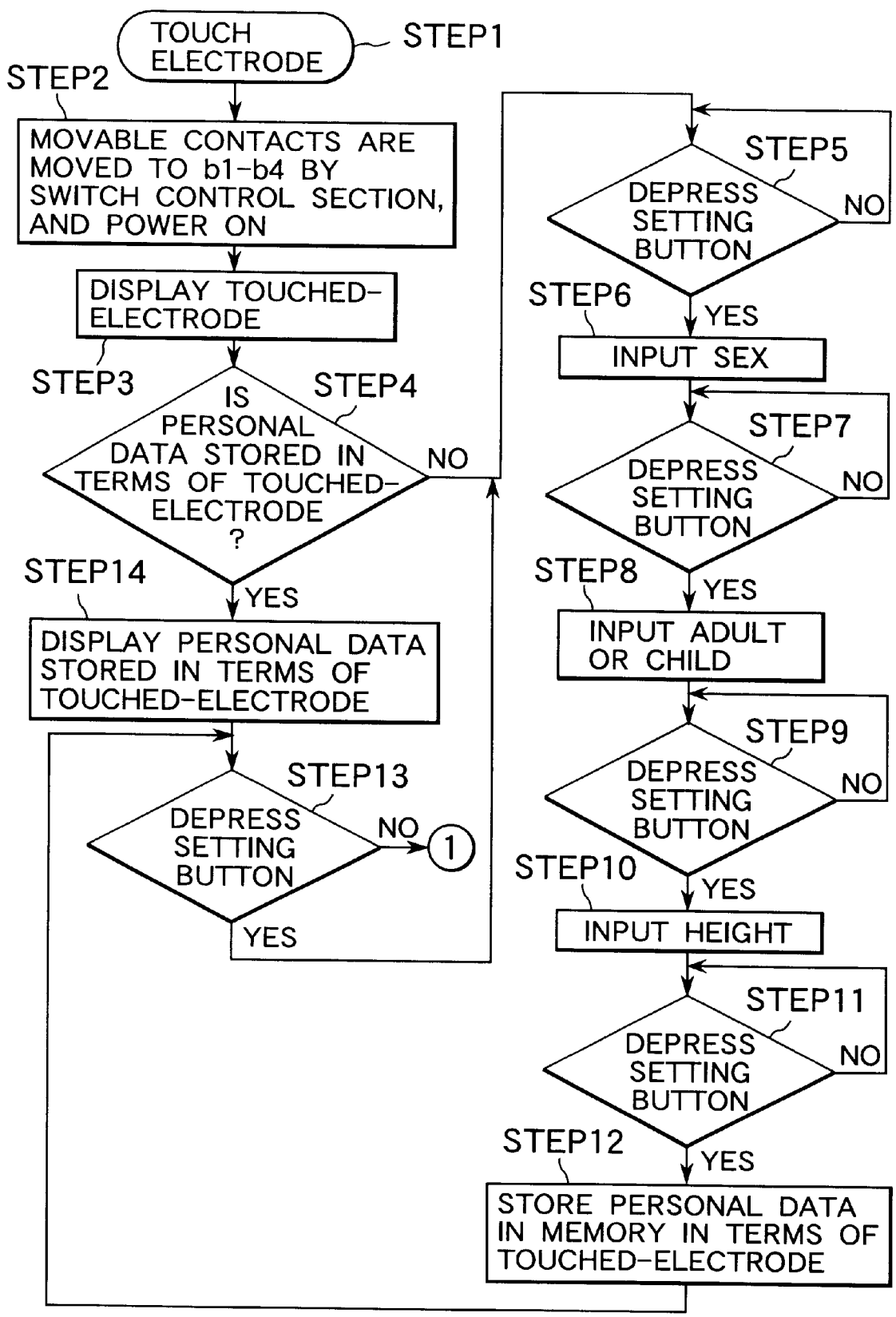
FIG. 4 is a flow chart showing a series of actions taken for entry of personal data in the body fat meter of FIG. 1.

Now, the manner in which the body fat meter 1 works is described by referring to FIGS. 1 to 5. The operation begins with the inputting of personal data as shown in FIG. 4.

An individual user can select one of the electrodes A, B, C and D for exclusive use in inputting his personal data. Assuming that the electrode A is selectively touched with finger or tiptoe (step 1), the movable contacts of the switches S1 to S4 are switched to the second stationary contacts b1 to b4 to make the power supply circuit 100 turn on (step 2), and then the sign A representing the touched electrode A appears on the display 2 (step 3).

Next, it is checked whether the personal data pertaining to the particular user is available from the memory in terms of the touched electrode A (step 4). In the affirmative case the stored personal data appear in the display 2 (step 14). In the negative case no personal data appears, and then, the user depresses the setting button 3 at step 5. In response to depression of the setting button 3 the marks representing male and female appear on the display 2. Either mark can be selected and inputted by means of the scroll-up button 4 or scroll-down button 5 (step 6).

The so inputted personal data on sex can be stored by depressing the setting button 3 (step 7). At the same time, the marks representing adult and child appear on the display 2. Likewise, either mark can be selected and inputted by means of the scroll-up button 4 or the scroll-down button 5 (step 8). At step 9 the so inputted personal data can be stored by depressing the setting button 3. At the same time, a predetermined height appears on the display 2, which height can be changed to the user's height by means of the scroll-up button 4 or the scroll-down button 5. When the user's height is reached to the user's height on the display 2, the setting button 3 is depressed so that the height may be stored. Thus, all the inputted personal data are stored in the particular location of the memory allotted to the electrode A (step 12).

At step 13 it is checked whether the setting button 3 was depressed or not. In the affirmative case the proceeding goes back to step 5, in which the personal data can be modified or reregistered. In the negative case the proceeding goes to step 20 (see FIG. 5), where the weight and bioelectrical impedance appearing between both feet are measured while the user stands on the body fat meter 1 with the heel and tiptoe of one foot on the electrodes C and A, and with those of the other foot on the electrodes D and B. The weight and bioelectrical impedance thus measured are used to calculate the body fat percentage (step 21). Then, the body fat percentage along with the measured weight appear on the display 2 (step 22).

After displaying the measured weight and the calculated body fat percentage on the display 2 for a predetermined length of time (step 23), the mode switching section 6 switches the mode of the measuring apparatus 1 from the measuring mode to the normal or stand-by mode. Specifically the switch control section 61 makes the movable contacts of the switches S1 to S4 move from the second stationary contacts b1 to b4 to the first stationary contacts a1 to a4 (step 24), and the central control section 101 shuts power off (step 25). Thus, the measurement is finished.

At step 10 the input of a predetermined number (e.g. "000") in place of the height puts the body fat meter in condition for measurement and presentation of one's weight rather than the bioelectrical impedance.

Figure 5:
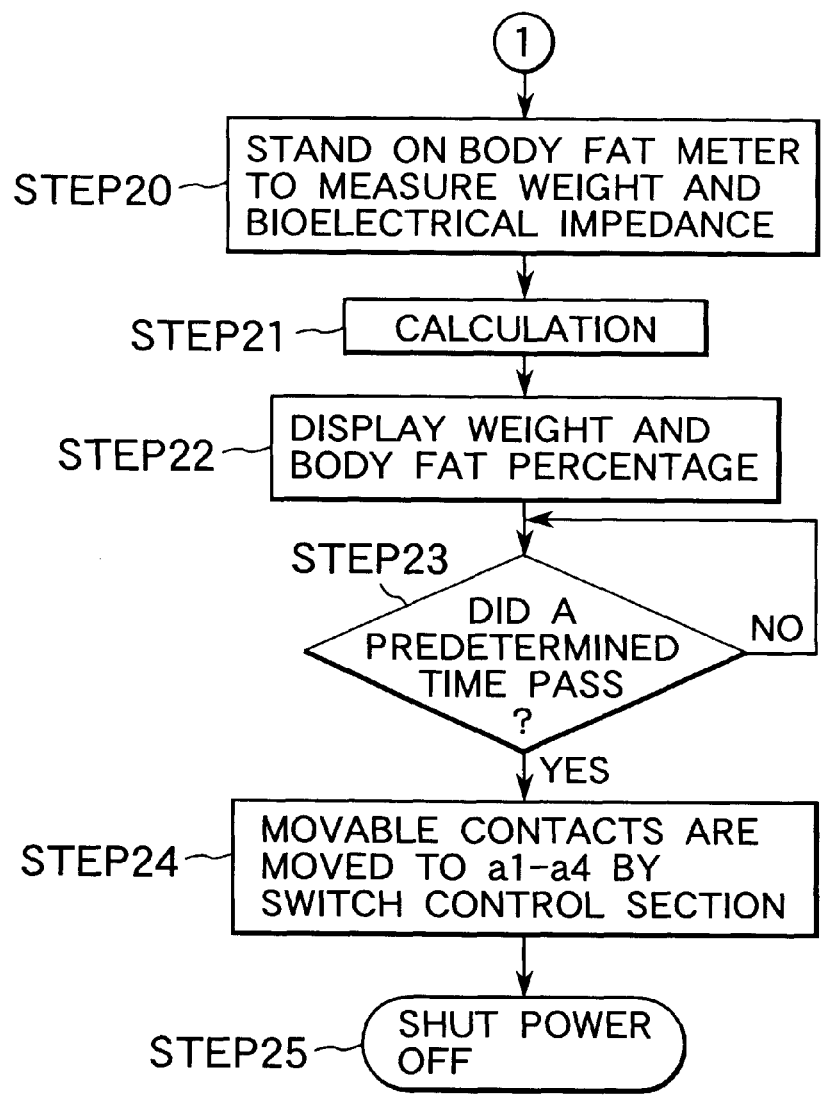
FIG. 5 is a flow chart showing a series of actions taken for a required measurement in the body fat meter of FIG. 1.

Although not shown in FIGS. 4 and 5, the central control section 101 includes an internal timer for counting the length of time for which an interruption continues in the course of entry of the personal data or in the course of a required measurement. In the event that the counted length of time exceeds a predetermined length of time, the electrodes A, B, C and D are connected to the touch-sensitive switch circuit 104 via the mode switching section 6, in which the movable contacts of the switches S1 to S4 are put in contact with the first stationary contacts a1 to a4, and power is shut off by the central control section 101.

The personal data are allowed to be stored in a selected location of the memory allotted to the touched one of the electrodes A, B, C and D. Thus, access is permitted to the stored personal data by touching the same electrode as used in inputting. Four users can store or retrieve their personal data from the memory of the body fat meter 1 by using the electrodes A, B, C and D allotted to their exclusive use.

The personal data may be inputted in a desired sequence other than that described above.

Figure 6:
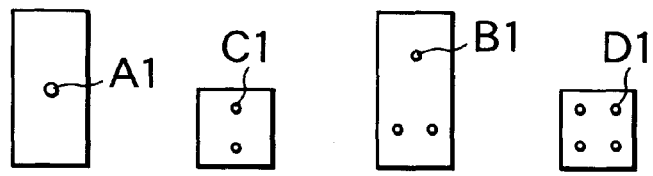
FIG. 6 shows the front view of another example of electrodes.
Figure 7:
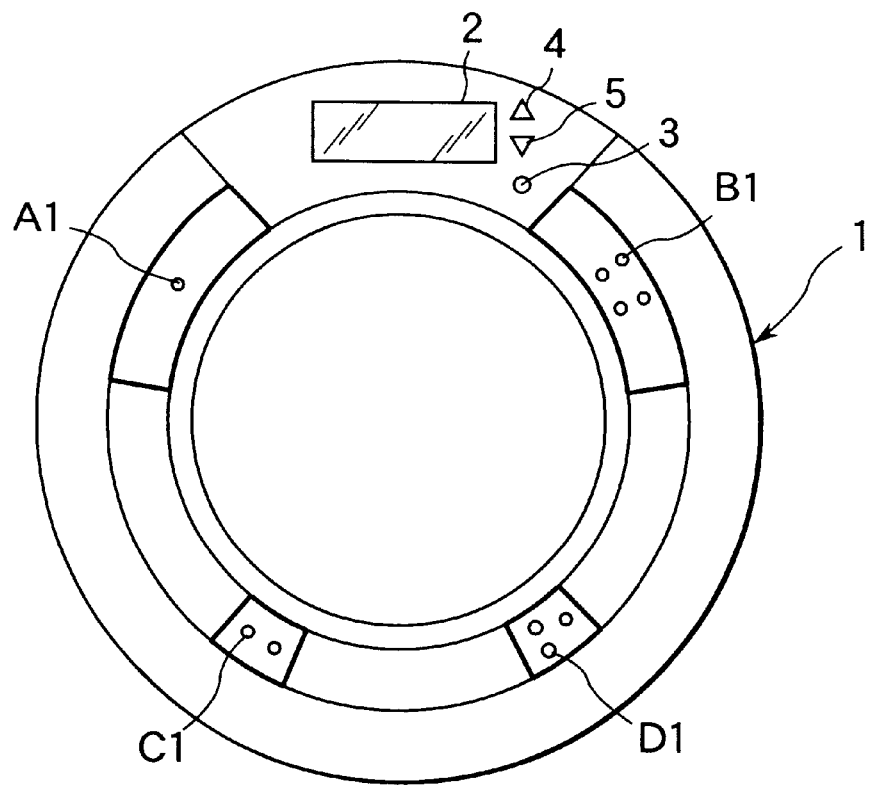
FIG. 7 shows the front view of a body fat meter according to a second embodiment of the present invention.
Figure 8:
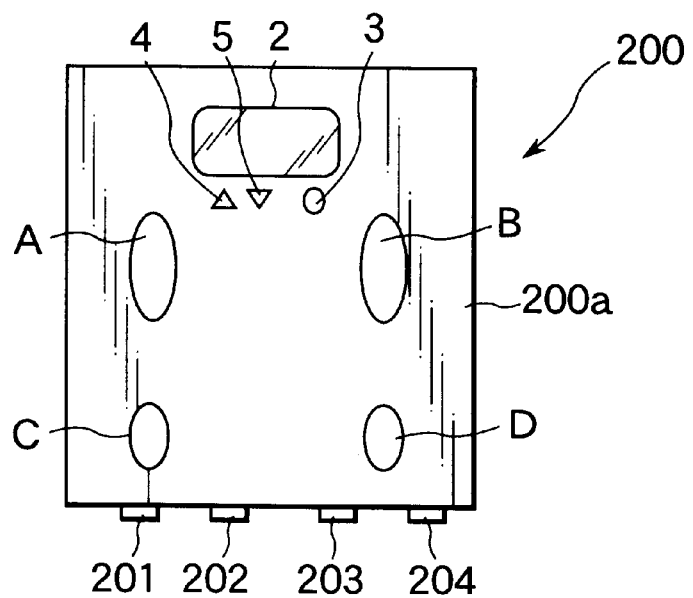
FIG. 8 shows the front view of a conventional body fat meter.

The electrodes A, B, C and D may have different number of protrusions for identification (see electrodes A1, B1, C1 and D1 in FIGS. 6 and 7). The electrodes A, B, C and D may be modified to be responsive to the touch for emitting light, thus facilitating confirmation by sight of the touched electrode.

The body fat meter 1 may be circular, and each electrode may have a fan-like shape or sector as shown in FIG. 7.

The present invention is described above as being applied to a weight scale type of body fat meter which measures the bioelectrical impedance appearing between both feet, but it can be equally applied to a hand-held type of body fat meter which measures the bioelectrical impedance appearing between both hands. Furthermore, it can be equally applied to body fat meter which measures the bioelectrical impedance appearing between hand and foot.

The present invention may be applied to a physical variable measuring apparatus having electrodes equipped therewith for measuring other physical variable than body fat percentage in terms of one's bioelectrical impedance, such as pulse rate meter or body water meter.

As may be understood from the above, a body fat meter according to the present invention is simplified in structure, permitting a required control to be carried out by using its electrodes to store or retrieve the personal data. In measuring the retrieval of personal data can be easily effected simply by touching selected electrodes, which is easier than depressing of selected individual keys as in the conventional body fat meter. The body fat meter can be stand on the floor with any one of its sides down without fear of turning power on; the body fat meter has no switch arranged on every side.

What is claimed is:

1. A bioelectrical impedance measuring apparatus comprising a personal data input unit for inputting personal data and a plurality of electrodes for measuring bioelectrical impedance, characterized in that it comprises:
    at least one memory area for storing said personal data; and
    a control device for storing said personal data in said memory area when any of said electrodes is touched or for retrieving said personal data from said memory area when any of said electrodes is touched.

2. A bioelectrical impedance measuring apparatus according to claim 1 wherein said control device is for storing said personal data in said memory area when said personal data is not available from said memory area when any of said electrodes is touched.

3. A bioelectrical impedance measuring apparatus according to claim 1 wherein said control device is for retrieving said personal data from said memory area when said personal data is available from said memory area when any of said electrodes is touched.

4. A bioelectrical impedance measuring apparatus according to claim 1 wherein said control device is for storing said personal data in said memory area corresponding to a selected electrode when said personal data is not available from said memory area when said selected electrode is touched.

5. A bioelectric impedance measuring apparatus according to claim 1 wherein said control device is for retrieving said personal data from said memory area corresponding to a selected electrode when said personal data is available from said memory area when said selected electrode is touched.

6. A bioelectric measuring apparatus according to any of claim 1 to 5 wherein it further comprises a power switch device responsive to a touch to any of said electrodes for turning power on.

7. A bioelectrical impedance measuring apparatus according to any of claim 1 to 5 wherein it further comprises a weight scale and a display, said control device being responsive to the inputting of a predetermined number in place of the height via said personal data input unit for permitting said weight scale to measure the weight alone and for permitting said display to show the so measured weight alone.

8. A bioelectrical impedance measuring apparatus according to any of claim 1 to 5 wherein it comprises:
    a bioelectrical impedance measuring circuit which measures the bioelectrical impedance appearing between selected points of a living body, on which points said electrodes are attached;
    a touch-sensitive switch circuit which is responsive to a touch to any one of said electrodes for making weak current flow through the touched electrode; and
    a mode switching device which switches the connection of said electrodes from said bioelectrical impedance measuring circuit to said touch-sensitive switch circuit or inversely.

9. A bioelectrical impedance measuring apparatus according to claim 1 comprising:
    a bioelectrical impedance measuring circuit which measures the bioelectrical impedance appearing between selected points of a living body, on which points said electrodes are attached;
    a touch-sensitive switch circuit which is responsive to a touch to any one of said electrodes for making weak current flow through the touched electrode; and
    a mode switching device which switches the connection of said electrodes from said bioelectrical impedance measuring circuit to said touch-sensitive switch circuit or inversely,
    wherein said control device includes an internal timer for counting the length of time for which an interruption continues in the course of entry of the personal data or in the course of measurement; and
    said control device is responsive to the length of time thus measured exceeding a predetermined length of time for making said electrodes to be connected to said touch-sensitive switch circuit via said mode switching device, and shutting power off.

* * * * *